US011490863B2

(12) United States Patent
Shin et al.

(10) Patent No.: US 11,490,863 B2
(45) Date of Patent: Nov. 8, 2022

(54) APPARATUS AND METHOD FOR ESTIMATING BIO-INFORMATION, AND APPARATUS FOR SUPPORTING ESTIMATION OF BIO-INFORMATION

(71) Applicant: SAMSUNG ELECTRONICS CO., LTD., Suwon-si (KR)

(72) Inventors: Eui Seok Shin, Yongin-si (KR); Chang Mok Choi, Suwon-si (KR); Byung Hoon Ko, Hwaseong-si (KR); Jong Wook Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 793 days.

(21) Appl. No.: 16/359,468

(22) Filed: Mar. 20, 2019

(65) Prior Publication Data

US 2020/0121259 A1 Apr. 23, 2020

(30) Foreign Application Priority Data

Oct. 19, 2018 (KR) ........................ 10-2018-0125136

(51) Int. Cl.
*A61B 5/00* (2006.01)
*A61B 5/024* (2006.01)

(52) U.S. Cl.
CPC .......... *A61B 5/7278* (2013.01); *A61B 5/0053* (2013.01); *A61B 5/02433* (2013.01);
(Continued)

(58) Field of Classification Search
CPC ............ A61B 5/02433; A61B 5/02416; A61B 5/14552; A61B 5/0053; A61B 5/441; A61B 5/6843
See application file for complete search history.

(56) References Cited

U.S. PATENT DOCUMENTS

| | | | | |
|---|---|---|---|---|
| 5,601,079 A * | 2/1997 | Wong | ................. | A61B 5/14532 600/476 |
| 5,623,933 A * | 4/1997 | Amano | ............. | A61B 5/02007 600/500 |

(Continued)

FOREIGN PATENT DOCUMENTS

| | | |
|---|---|---|
| DE | 10 2006 026 173 A1 | 12/2007 |
| EP | 3 111 834 A1 | 1/2017 |

(Continued)

OTHER PUBLICATIONS

Ahn, Jae Mok PhD., "New Aging Index using Signal Features of Both Photoplethysmograms and Acceleration Plethysmograms", Healthcare Informatics Research, vol. 23, No. 1, Jan. 1, 2017, pp. 53-59, XP055436243. (7 pages total).

(Continued)

*Primary Examiner* — Oommen Jacob
(74) *Attorney, Agent, or Firm* — Sughrue Mion, PLLC

(57) ABSTRACT

An apparatus for estimating bio-information based on pulse wave signals of multiple wavelengths is disclosed. The bio-information estimating apparatus may include: a sensor part comprising a pulse wave sensor configured to measure a multi-wavelength pulse wave signal at a first point in time when a first pressure is applied from an object to the sensor part and at a second point in time when a second pressure is applied from the object to the sensor part; and a processor configured to estimate bio-information based on a difference between the multi-wavelength pulse wave signal measured at the first pressure and the multi-wavelength pulse wave signal measured at the second pressure.

20 Claims, 13 Drawing Sheets

(52) U.S. Cl.
CPC .......... *A61B 5/02438* (2013.01); *A61B 5/441* (2013.01); *A61B 5/6843* (2013.01); *A61B 2560/045* (2013.01)

(56) References Cited

U.S. PATENT DOCUMENTS

| | | | | |
|---|---|---|---|---|
| 5,827,181 | A * | 10/1998 | Dias | A61B 5/0053 600/323 |
| 6,126,595 | A * | 10/2000 | Amano | A61B 5/02 600/490 |
| 6,990,364 | B2 | 1/2006 | Ruchti et al. | |
| 7,139,598 | B2 | 11/2006 | Hull et al. | |
| 7,179,228 | B2 | 2/2007 | Banet | |
| 8,078,243 | B2 | 12/2011 | Ediger et al. | |
| 8,121,671 | B2 | 2/2012 | Hull et al. | |
| 11,154,224 | B2 * | 10/2021 | Katra | A61B 5/6826 |
| 2002/0165439 | A1 * | 11/2002 | Schmitt | G01N 21/359 600/309 |
| 2004/0068163 | A1 | 4/2004 | Ruchti et al. | |
| 2004/0186363 | A1 * | 9/2004 | Smit | A61B 5/0071 600/317 |
| 2005/0148834 | A1 | 7/2005 | Hull et al. | |
| 2006/0009685 | A1 * | 1/2006 | Finarov | A61B 5/0053 600/344 |
| 2006/0211928 | A1 | 9/2006 | Hull et al. | |
| 2007/0043281 | A1 * | 2/2007 | Fine | A61B 5/1455 600/335 |
| 2007/0088205 | A1 | 4/2007 | Hull et al. | |
| 2009/0306521 | A1 * | 12/2009 | Ermakov | A61B 5/0075 600/587 |
| 2011/0046464 | A1 * | 2/2011 | Debreczeny | A61B 5/6843 600/335 |
| 2012/0065484 | A1 | 3/2012 | Hull et al. | |
| 2014/0213865 | A1 * | 7/2014 | Kobayashi | A61B 5/0053 600/323 |
| 2014/0249424 | A1 * | 9/2014 | Fan | A61B 5/0255 600/473 |
| 2015/0168205 | A1 * | 6/2015 | Lee | H04M 1/0254 177/1 |
| 2016/0089088 | A1 | 3/2016 | Kim et al. | |
| 2016/0135691 | A1 | 5/2016 | Dripps et al. | |
| 2017/0000350 | A1 | 1/2017 | Kwon et al. | |
| 2017/0042484 | A1 | 2/2017 | Chong et al. | |
| 2017/0071550 | A1 | 3/2017 | Newberry | |
| 2017/0086753 | A1 | 3/2017 | Presura et al. | |
| 2017/0172430 | A1 | 6/2017 | Zhao et al. | |
| 2018/0177413 | A1 | 6/2018 | Kwon et al. | |
| 2018/0303358 | A1 | 10/2018 | Presura et al. | |
| 2019/0313979 | A1 | 10/2019 | Kang et al. | |
| 2019/0387985 | A1 | 12/2019 | Kang et al. | |
| 2020/0121259 | A1 * | 4/2020 | Shin | A61B 5/441 |
| 2020/0146568 | A1 * | 5/2020 | Park | A61B 5/02116 |
| 2020/0229743 | A1 * | 7/2020 | Choi | A61B 5/681 |

FOREIGN PATENT DOCUMENTS

| | | | |
|---|---|---|---|
| EP | 3 552 539 | A1 | 10/2019 |
| EP | 3 583 891 | A1 | 12/2019 |
| KR | 10-2013-0014646 | A | 2/2013 |
| KR | 10-1724282 | B1 | 4/2017 |
| WO | 02/065090 | A2 | 8/2002 |
| WO | 2017/055307 | A1 | 4/2017 |
| WO | 2017/152098 | A1 | 9/2017 |

OTHER PUBLICATIONS

Communication dated Feb. 17, 2020 by the European Patent Office in counterpart European Patent Application No. 19173575.2.

Pedro Santos et al., "Photoplethysmographic Logger with Contact Force and Hydrostatic Pressure Monitoring", Bioengineering (Enbeng), 2013 IEEE 3rd Portuguese Meeting In, IEEE, Feb. 20, 2013, pp. 1-6, XP032410163. (6 pages total).

X F Teng et al., "The effect of contacting force on photoplethysmographic signals", Physiological Measurement, Institute of Physics Publishing, Bristol, GB, vol. 25, No. 5, Oct. 1, 2004, pp. 1323-1335, XP020074200. (13 pages total).

Search Report dated Jul. 18, 2019 by the European Patent Office in counterpart European Patent Application No. 19173575.2.

* cited by examiner

APPARATUS AND METHOD FOR ESTIMATING BIO-INFORMATION, AND APPARATUS FOR SUPPORTING ESTIMATION OF BIO-INFORMATION

CROSS-REFERENCE TO RELATED APPLICATION(S)

This application claims priority from Korean Patent Application No. 10-2018-0125136, filed on Oct. 19, 2018, in the Korean Intellectual Property Office, the disclosure of which is incorporated herein by reference in its entirety.

BACKGROUND

1. Field

Apparatuses and methods consistent with example embodiments relate to estimating bio-information based on pulse wave signals having multiple wavelengths.

2. Description of the Related Art

With the aging of body tissues or under long-term exposure to high concentrations of glucose, proteins such as collagen in body tissues or blood vessels become glycated by non-enzymatic reactions. These glycated proteins are called Advanced Glycation End products (AGEs). As the amount of AGEs in the body tissues increases, elasticity of the body tissues is reduced as a result of protein denaturation. That is, when the glucose concentration in the blood remains high for a long period of time, glycation of proteins in the blood vessels is accelerated, reducing elasticity of the walls of blood vessels with glycated proteins, and increasing vascular permeability, as well as oxidative stress and inflammatory factors in the blood vessels.

Such protein denaturation in the blood vessels may be a factor in increasing cardiovascular disease risk such as arteriosclerosis and high blood pressure. Furthermore, the increase in glycated proteins in the blood vessels includes increased glycation of collagen proteins in tissues of the dermal layer. Once protein glycation occurs, autofluorescence increases, which emanates when infrared light is radiated, such that a degree of glycation of proteins may be estimated by measuring the autofluorescence emanating when infrared light is radiated, and cardiovascular disease risk may be predicted based on the estimation.

SUMMARY

An aspect of an example embodiment, there is provided a bio-information estimating apparatus including: a sensor part comprising a pulse wave sensor configured to measure a multi-wavelength pulse wave signal at a first point in time when a first pressure is applied from an object to the sensor part and at a second point in time when a second pressure is applied from the object to the sensor part; and a processor configured to estimate bio-information based on a difference between the multi-wavelength pulse wave signal measured at the first pressure and the multi-wavelength pulse wave signal measured at the second pressure.

The pulse wave sensor may include a light source configured to emit light of multiple wavelengths onto the object, and a detector configured to detector light scattered or reflected from the object.

In this case, at least one of the first pressure and the second pressure comprises contact pressure between the sensor part and the object, which occurs when the object touches the sensor part without exerting force to the sensor part.

The processor may obtain a first value based on the multi-wavelength pulse wave signal at the first pressure and a predefined function, and a second value based on the multi-wavelength pulse wave signal at the second pressure and the predefined function, and may estimate the bio-information based on the first value and the second value.

In this case, the function may include at least one of a logarithmic function and a linear combination function.

The multi-wavelength pulse wave signal may include a first pulse wave signal of a first wavelength and a second pulse wave signal of a second wavelength. The processor may calculate a ratio between an intensity of the first pulse wave signal and an intensity of the second pulse wave signal for each of the first and the second pressures, and may obtain the first value and the second value by applying the function to the calculated ratio.

The processor may extract a direct current (DC) component from the first and the second pulse wave signals, and may obtain a statistical value of the DC component as the intensity of the first and the second pulse wave signals.

The first wavelength may be shorter than the second wavelength.

The processor may calculate a difference between the first value and the second value, and may apply a bio-information estimation model to the calculated difference.

The bio-information may include at least one of a degree of skin tissue aging and a biological age.

The processor may provide guidance on at least one of the first pressure, the second pressure, and contact pressure between the object and the pulse wave sensor.

Upon receiving a request for estimating bio-information, the processor may guide the object to touch the pulse wave sensor with the first pressure for a first period of time; and after a lapse of the first period of time, the processor may guide the object to touch the pulse wave sensor with the second pressure for a second period of time.

The processor may obtain the contact pressure between the object and the pulse wave sensor, and may provide guidance on the contact pressure.

The sensor part may further include a force sensor configured to measure an intensity of force applied by the object when the object touches the pulse wave sensor, and an area sensor configured to measure a contact area between the object and the pulse wave sensor, wherein the processor may obtain the contact pressure based on the intensity of force and the contact area.

In addition, the bio-information estimating apparatus may further include an output interface configured to output a processing result of the processor.

The processor may be further configured to generate a bio-information estimation model based on a plurality of first multi-wavelength pulse wave signals measured from a plurality of users when the first pressure is applied to the sensor part, a plurality of second multi-wavelength pulse wave signals measured from the plurality of users when the second pressure is applied to the sensor part, and information on a degree of aging of the plurality of users.

For the plurality of users, the processor may be further configured to obtain a first value based on the first multi-wavelength pulse wave signals at the first pressure and a logarithmic function, and a second value based on the second multi-wavelength pulse wave signals at the second pressure and the logarithmic function, and generate the bio-information estimation model by analyzing a correlation between a difference between the first value and the second value and the degree of aging.

According to an aspect of another example embodiment, there is provided a bio-information estimating method including: measuring a first multi-wavelength pulse wave signal at a first point in time when a first pressure is applied from an object to a sensor; measuring a second multi-wavelength pulse wave signal at a second point in time when a second pressure is applied from the object to the sensor; and estimating bio-information based on a difference between the first multi-wavelength pulse wave signal measured at the first pressure and the second multi-wavelength pulse wave signal measured at the second pressure.

The estimating of the bio-information may include: obtaining a first value based on the first multi-wavelength pulse wave signal at the first pressure and a predefined function; and obtaining a second value based on the second multi-wavelength pulse wave signal at the second pressure and the predefined function.

In this case, the function may include at least one of a logarithmic function and a linear combination function.

The multi-wavelength pulse wave signal may include a first pulse wave signal of a first wavelength and a second pulse wave signal of a second wavelength, The obtaining of the first value and the second value may include applying the function to a ratio between an intensity of the first pulse wave signal and an intensity of the second pulse wave signal.

The obtaining of the first value and the second value may include extracting a DC component from the first and the second pulse wave signals, and obtaining a statistical value of the DC component as the intensity of the first and the second pulse wave signals.

The estimating of the bio-information may include: calculating a difference between the first value and the second value; and applying a bio-information estimation model to the calculated difference.

In addition, the bio-information estimating method may further include: guiding the object to touch the pulse wave sensor with the first pressure for a first period of time; and after a lapse of the first period of time, guiding the object to touch the pulse wave sensor with the second pressure for a second period of time.

Furthermore, the bio-information estimating method may further include: obtaining contact pressure between the object and the pulse wave sensor; and providing guidance on the obtained actual contact pressure.

Moreover, the bio-information estimating method may further include outputting a processing result of the processor.

According to an aspect of another example embodiment, there is provided an apparatus for supporting estimation of bio-information, the apparatus including: an information collector configured to collect multi-wavelength pulse wave signals measured at a first pressure, multi-wavelength pulse wave signals measured at a second pressure, and information on a degree of aging, from a plurality of users; and a processor configured to generate a bio-information estimation model based on the multi-wavelength pulse wave signals measured at the first pressure, the multi-wavelength pulse wave signals measured at the second pressure, and the information on the degree of aging, for the plurality of users.

For the plurality of users, the processor may obtain a first value based on the multi-wavelength pulse wave signals at the first pressure and a logarithmic function, and a second value based on the multi-wavelength pulse wave signals at the second pressure and the logarithmic function, and may generate the bio-information estimation model by analyzing a correlation between a difference between the first value and the second value and the degree of aging.

The processor may calculate a ratio between an intensity of a pulse wave signal of a first wavelength and an intensity of a pulse wave signal of a second wavelength for each of the pressures, and may obtain the first value and the second value by applying the logarithmic function to the calculated ratio.

The information on the degree of aging may include at least one of a user's biological age and skin fluorescence.

In addition, the apparatus for supporting estimation of bio-information may further include a communication interface configured to transmit the bio-information estimation model to a bio-information estimating apparatus.

Furthermore, the apparatus for supporting estimation of bio-information may further include a memory configured to store at least one of the collected multi-wavelength pulse wave signals, the information on the degree of aging, and the generated bio-information estimation model.

BRIEF DESCRIPTION OF THE DRAWINGS

The above and/or other aspects will be more apparent by describing certain example embodiments, with reference to the accompanying drawings, in which.

DETAILED DESCRIPTION

Figure 1A:
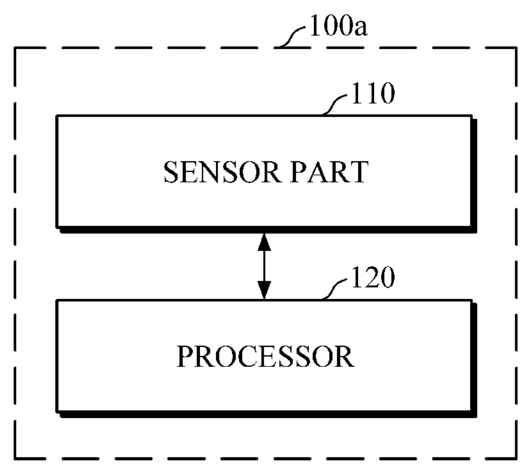
FIGS. 1A and 1B are block diagrams illustrating a bio-information estimating apparatus according to example embodiments.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module' etc., should be understood as a unit that performs at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, embodiments of a bio-information estimating apparatus and a bio-information estimating method will be described in detail with reference to the accompanying drawings.

Figure 1B:
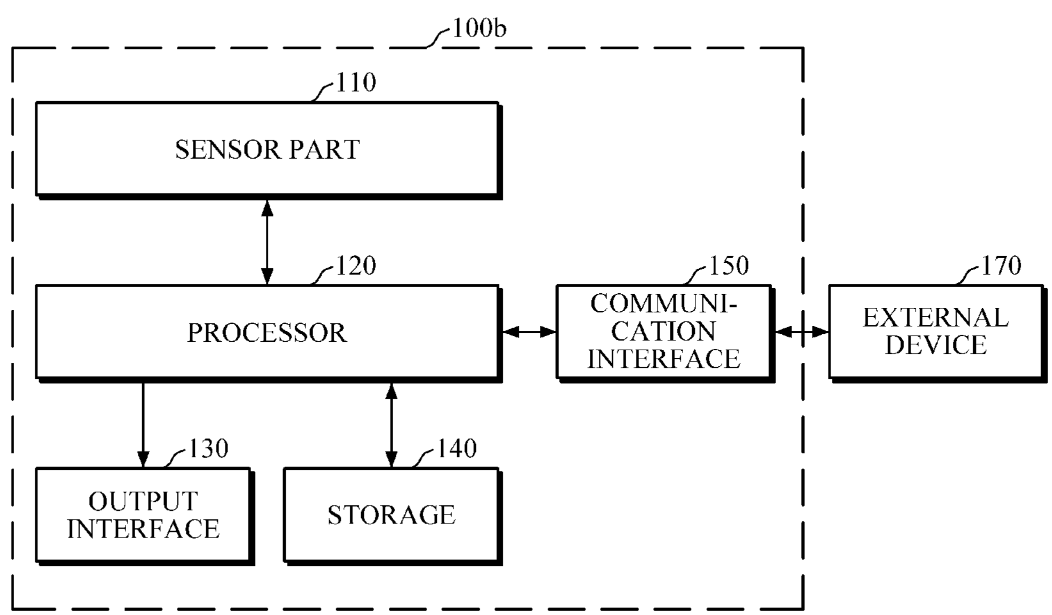
Figure 2A:
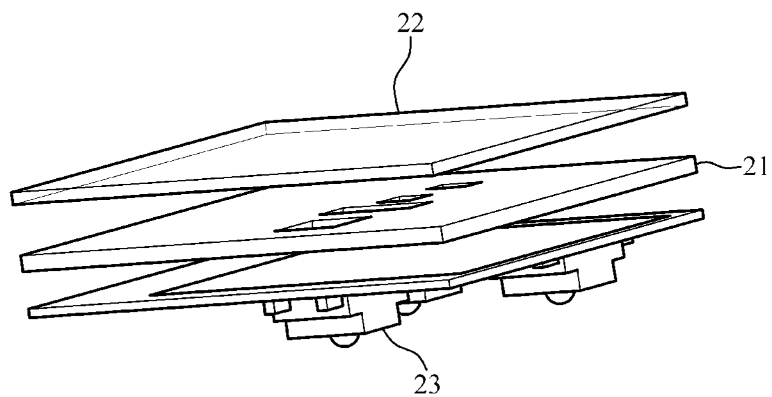
FIGS. 2A and 2B are diagrams illustrating a structure of a sensor according to an example embodiment.
Figure 2B:
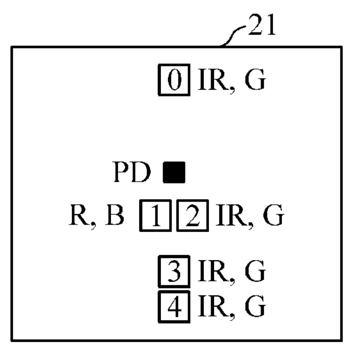

FIGS. 1A and 1B are block diagrams illustrating a bio-information estimating apparatus according to example embodiments. FIGS. 2A and 2B are diagrams illustrating a structure of a sensor according to an example embodiment.

The bio-information estimating apparatuses 100*a* and 100*b* may be embedded in a terminal, such as a smartphone, a tablet PC, a desktop computer, a laptop computer, and the like, or in a wearable device that may be worn on an object. In this case, examples of the wearable device may include a wristwatch-type wearable device, a bracelet-type wearable device, a wristband-type wearable device, a ring-type wearable device, a glasses-type wearable device, a hairband-type wearable device, or the like, but the wearable device is not limited thereto, and may also be embedded in a medical device manufactured for use in medical institutions to measure and analyze bio-information.

Referring to FIGS. 1A and 1B, each of the bio-information estimating apparatuses 100*a* and 100*b* includes a sensor part 110 and a processor 120.

The sensor part 110 may measure various signals from an object when the object touches the sensor part 110. In particular, the object may be a body part which comes into contact with or is adjacent to the sensor part 110, and may be a body part where pulse waves may be easily measured. For example, the object may be an area of skin on the wrist that is adjacent to the radial artery or a human skin area through which veins or capillaries pass. However, the object is not limited thereto, and may be peripheral body portions, such as fingers, toes, and the like, which have a high density of blood vessels.

Referring to FIG. 2A, the sensor part 110 may include a pulse wave sensor 21 for measuring a pulse wave signal having multiple wavelengths from the object when the object touches the sensor part 110. The pulse wave signal may include a photoplethysmogram (PPG) signal. In particular, the multiple wavelengths may include two or more of an infrared wavelength, a green wavelength, a blue wavelength, and a red wavelength.

Referring to FIG. 2B, the pulse wave sensor 21 may include one or more light sources 0-4 and a detector PD which are arranged on a substrate. The arrangement of the light sources 0-4 and the detector PD is not limited thereto, and may be modified in various ways according to the size of the pulse wave sensor, computing performance of the bio-information estimating apparatus 100, and the like. Each of the light sources 0-4 may emit light of different wavelengths onto an object, and may include a light emitting diode (LED), a laser diode (LD), a fluorescent body, and the like. The detector PD may include one or more pixels, each of which includes a photo diode, a photo transistor (PTr), an image sensor, and the like, which detect light reflected or scattered from the object and convert the detected light into an electric signal. However, examples of the light sources 0-4 and the detector PD are not limited thereto.

Referring to FIG. 2A, the sensor part 110 may include: an area sensor 22 which is disposed above the pulse wave sensor 21 and measures a contact area when the object touches the area sensor 22; and a force sensor 23 which is disposed below the pulse wave sensor 21 and measures an intensity of force applied by the object when the object touches the area sensor 22. The area sensor 22 may be made of a transparent material so that light may be transmitted therethrough. The area sensor 22 may be formed as a touch panel for touch input.

The processor 120 may be electrically connected to the sensor part 110. The processor 120 may control the sensor part 110 in response to a request for estimating bio-information, and may estimate bio-information by using a multi-wavelength pulse wave signal received from the sensor part 110. In particular, bio-information may include a biological age or a degree of tissue aging of a user, and the like, but is not limited thereto.

For example, the processor 120 may provide guidance on contact pressure to a user so that the sensor part 110 may measure multi-wavelength pulse wave signals at two or more different contact pressures. Once the sensor part 110 measures multi-wavelength pulse wave signals at each of the contact pressures, the processor 120 may estimate a change between the multi-wavelength pulse wave signals measured at each of the contact pressures, and may estimate bio-information based on the estimated change between the pulse wave signals.

In an example embodiment, the processor 120 may prompt the user to press down the sensor part 110 with gradually increasing force while the sensor part 110 is measuring a multi-wavelength pulse wave signal, and may determine a change in the force exerted onto the sensor part 110 in relation to a change in the value of the multi-wavelength pulse wave signal. The processor 120 may continuously measure the change in the force exerted onto the sensor part 110, or may discretely measure the force at a plurality of different times to determine the change in the force exerted onto the sensor part 110.

Referring to FIG. 1B, the bio-information estimating apparatus 100*b* may further include an output interface 130, a memory 140, and a communication interface 150, in addition to the sensor part 110 and the processor 120.

The output interface 130 may output processing results of the sensor part 110 and the processor 120. For example, the output interface 130 may visually output an estimated bio-information value using a display screen. Alternatively, the output interface 130 may output the estimated bio-information value in a non-visual manner through voice, vibrations, tactile sensation, and the like using a speaker, a haptic vibration motor, and the like. The output interface 130 may divide a display area into two or more areas according to a setting, in which the output interface 130 may output, in a first area, a graph of a pulse wave signal having multiple wavelengths which is used for estimating bio-information, a bio-information estimation result, and the like, and may output a bio-information estimation history in the form of a graph and the like in a second area. In this case, if an estimated bio-information value falls outside a normal range, the output interface 130 may output warning information in various manners, such as highlighting an abnormal value in red and the like, displaying the abnormal value along with a normal range, outputting a voice warning message, adjusting a vibration intensity, and the like.

The memory 140 may store processing results of the sensor part 110 and the processor 120. Further, the memory 140 may store various criteria required for estimating bio-information. For example, the criteria may include user feature information such as a user's biological age, gender, health condition, and the like. In addition, the criteria may also include information on first pressure and second pressure, a function for estimating a pulse wave signal change, and the like, but are not limited thereto.

In particular, the memory 140 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but the storage medium is not limited thereto.

The communication interface 150 may communicate with an external device 170 using wired or wireless communication techniques under the control of the processor 120, and may transmit and receive various data to and from the external device 170. For example, the communication interface 150 may transmit a bio-information estimation result to the external device 170, and may receive various criteria (e.g., a bio-information estimation model) which are required for estimating bio-information, from the external device 170. Examples of the external device 170 may include an apparatus for supporting estimation of bio-information, and an information processing device such as a smartphone, a tablet PC, a desktop computer, a laptop computer, and the like. For example, the processor 120 may determine whether it is required to update a bio-information estimation model based on a predetermined estimation interval, a change in user characteristics, a bio-information estimation result, and the like. The processor 120 may control the communication interface 150 to receive a bio-information estimation model from the apparatus for supporting estimation of bio-information.

Examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

Figure 3:
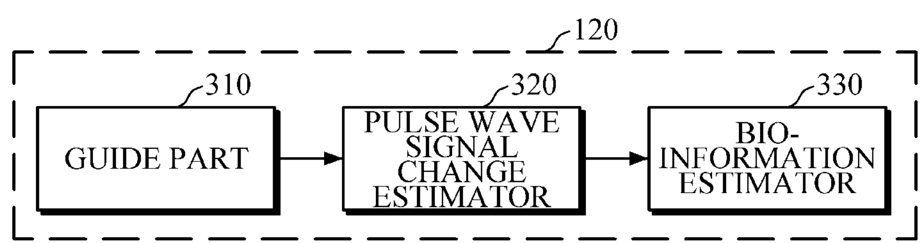
FIG. 3 is a block diagram of a processor according to according to an example embodiment.
Figure 4:
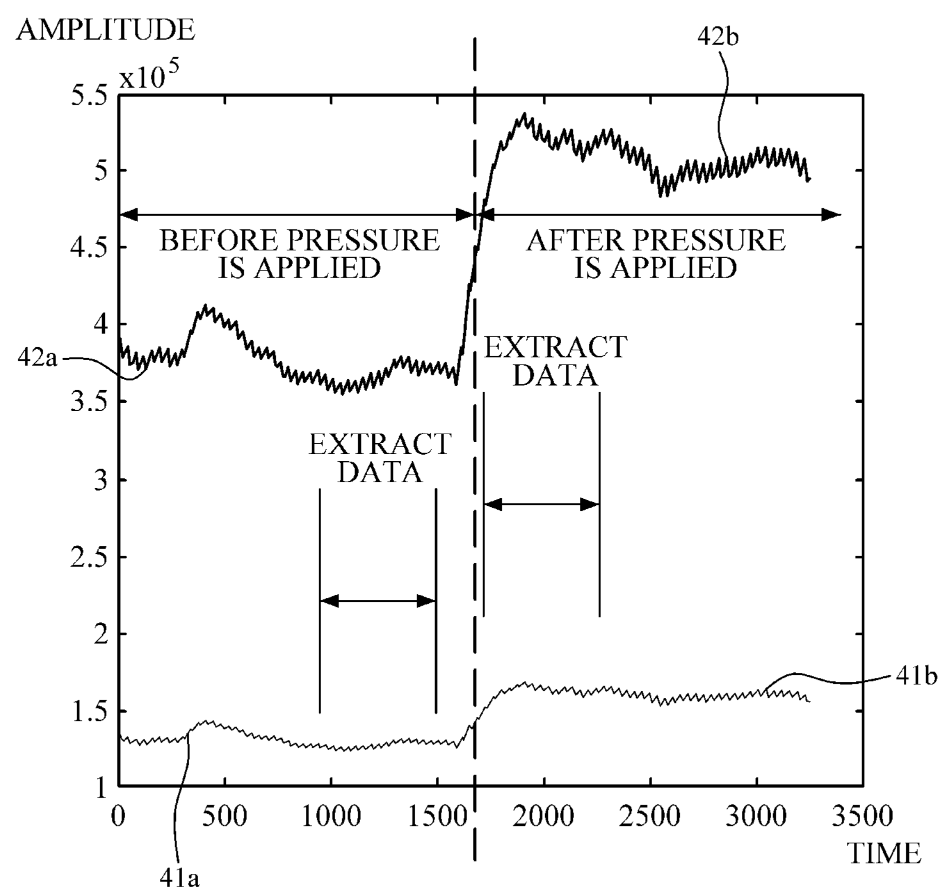
FIG. 4 is a diagram explaining an example of estimating bio-information based on multi-wavelength pulse wave signals before and after pressure is applied.

FIG. 3 is a block diagram of a processor according to example embodiments of FIGS. 1A and 1B. FIG. 4 is a diagram explaining an example of estimating bio-information.

Referring to FIG. 3, the processor 120 includes a guide part 310, a pulse wave signal change estimator 320, and a bio-information estimator 330.

Upon receiving a request for estimating bio-information, the guide part 310 may provide guidance on contact pressure to a user. For example, while a user touches the sensor part 110 with an object, the guide part 310 may guide a user to press the sensor part 110 with a first pressure for a first period of time (e.g., 18 seconds). Then, after a lapse of the first period of time, the guide part 310 may guide the user to press the sensor part 110 with a second pressure for a second period of time (e.g., 18 seconds). The first pressure and the second pressure may be set to a predetermined range of pressure levels. The first pressure may include contact pressure in a state where the user touches the sensor part 110 with an object without applying force to the sensor part 110; the second pressure may include contact pressure in a state where the user applies force, which is higher than or equal to a predetermined threshold, while the user touches the sensor part 110 with an object; and vice versa. The contact pressure may arise from the contact between two different bodies. The term "contract pressure" may be also referred to "contact stress" or "Hertz contact stress." In particular, the first period of time and the second period of time may be continuous or discontinuous periods of time.

The output interface 130 may visually and/or non-visually output information on the first pressure and the second pressure according to guidance of the guide part 310. For example, in the case where a user touches the sensor part 110 with an object to estimate bio-information, the output interface 130 may visually display a range of the first pressure for a first period of time through a display screen; and after a lapse of the first period of time, the output interface 130 may visually display a range of the second pressure for a second period of time through the display screen. In particular, the output interface 130 may display the range of the first pressure and the range of the second pressure in different colors, so that a user may easily recognize a time to change pressure after a lapse of the first period of time. Alternatively, at a time after the first period of time elapses, the output interface 130 may output voice, such as "please apply pressure from now on", through a voice output device such as a speaker, or may generate vibrations, tactile sensation, and the like using a haptic module.

In addition, when a user touches the sensor part 110 with an object and applies pressure thereto according to guidance of the guide part 310, the guide part 310 may obtain actual contact pressure of the object for each time. Further, the guide part 310 may provide guidance on the obtained actual contact pressure, so that the user may correctly maintain the first pressure and the second pressure. For example, when a user touches the sensor part 110 with an object and applies pressure to the sensor part 110, the guide part 310 may obtain contact pressure by using an intensity of force measured by a force sensor and a contact area measured by an area sensor.

The output interface 130 may display information on the first pressure and the second pressure along with the actual contact pressure, so that a user may easily recognize a difference between a pressure level to be applied and actual contact pressure. Further, in the case where the first pressure is different from the second pressure by more than a predetermined threshold, the output interface 130 may output voice or vibrations to allow the user to check a current contact state.

The pulse wave signal change estimator 320 may estimate a change between a multi-wavelength pulse wave signal at the first pressure and a multi-wavelength pulse wave signal at the second pressure, which are measured by the sensor part 110.

For example, referring to FIG. 4, the pulse wave signal change estimator 320 may extract data of pulse wave signals 41*a* and 42*a* of each wavelength, which are measured at the first pressure in a state where no pressure is applied by an object for a first period of time (e.g., approximately 0 to 1700 seconds), and may obtain the intensity of the pulse wave signals 41*a* and 42*a* of each wavelength. Likewise, the pulse wave signal change estimator 320 may extract data of pulse wave signals 41*b* and 42*b* of each wavelength, which are measured at the second pressure in a state where a pressure level higher than or equal to a predetermined threshold is applied by the object for a second period of time (e.g., approximately 1700 to 3300 seconds), and may obtain the intensity of the pulse wave signals 41*b* and 42*b* of each wavelength. In an example embodiment, the sensor part 110 may measure the pulse wave signals 41*a* and 42*a* while the output interface 130 outputs a message requesting the user to place his/her body part (e.g., finger) on the sensor part 110 without exerting force onto the sensor part 110. The sensor part 110 may measure the pulse wave signals 41*b* and 42*b* when the pressure applied to the sensor part 110 reaches the predetermined threshold as a result of the output interface 130 outputting a message that provides guidance on an amount of pressure that the user needs to use to press the sensor part 110. For example, the output interface 130 may display a message requesting the user to press the sensor part 110 harder until a measurement value of the pressure applied to the sensor part reaches the predetermined threshold.

The pulse wave signal change estimator 320 may extract a direct current (DC) component from the pulse wave signals 41*a*, 42*a*, 41*b*, and 42*b* of each wavelength, and may obtain a statistical value (e.g., mean value) of the extracted DC component as the intensity of the pulse wave signals 41*a*, 42*a*, 41*b*, and 42*b*. The pulse wave signal change estimator 320 may extract the DC component by passing the pulse wave signals 41*a*, 42*a*, 41*b*, and 42*b* through a low-pass filter (LPF).

The pulse wave signal change estimator 320 may calculate a ratio between the intensity of a pulse wave signal of a first wavelength and the intensity of a pulse wave signal of a second wavelength for the first pressure, and may obtain a first value by inputting the calculated ratio into a predefined function. Further, the pulse wave signal change estimator 320 may calculate a ratio between the intensity of a pulse wave signal of a first wavelength and the intensity of a pulse wave signal of a second wavelength for the second pressure, and may obtain a second value by inputting the calculated ratio into a predefined function. In particular, the first wavelength may be a relatively short wavelength (e.g., a blue wavelength) and the second wavelength may be a relatively long wavelength (e.g., a green wavelength). The first wavelength and the second wavelength at the first pressure may be the same as the first wavelength and the second wavelength at the second pressure.

The following Equation 1 represents a logarithmic function for obtaining the first value and the second value, but is not limited thereto and may be defined as various functional equations such as a linear combination function, a non-linear combination function, and the like.

$$f_1 = -\log\left(\frac{I_{21}}{I_{11}}\right) \quad \text{[Equation 1]}$$

$$f_2 = -\log\left(\frac{I_{22}}{I_{12}}\right)$$

Herein, $f_1$ and $f_2$ denote the first value and the second value; $I_{11}$ and $I_{21}$ denote the intensities of pulse wave signals of the first wavelength and the second wavelength at the first pressure; and $I_{12}$ and $I_{22}$ denote the intensities of pulse wave signals of the first wavelength and the second wavelength at the second pressure.

Upon obtaining the first value $f_1$ and the second value $f_2$ for each pressure, the pulse wave signal change estimator 320 may calculate a difference $\Delta f$ between the first value $f_1$ and the second value $f_2$ (e.g., $\Delta f = f_2 - f_1$) as a pulse wave signal change for the first pressure $f_1$ and the second pressure $f_2$.

Once the pulse wave signal change estimator 320 calculates the difference $\Delta f$ between the first value $f_1$ and the second value $f_2$, the bio-information estimator 330 may estimate bio-information by applying a predefined bio-information estimation model. In particular, the bio-information estimation model may be a linear regression equation which represents a correlation between the calculated difference $\Delta f$ and a user's biological age or a degree of tissue aging. However, the bio-information estimation model is not limited thereto, and may be defined in various manners such as a non-linear regression equation and the like.

The following Equation 2 represents a simple linear function of a bio-information estimation model. Once the pulse wave signal change estimator 320 obtains the first value $f_1$ and the second value $f_2$ by using Equation 1, and calculates the difference $\Delta f$ between the first value $f_1$ and the second value $f_2$, the bio-information estimator 330 may estimate bio-information, such as a biological age or a degree of tissue aging of user, by inputting the obtained difference $\Delta f$ into an independent variable of the following Equation 2.

$$y = ax + b \quad \text{[Equation 2]}$$

Herein, y denotes an estimated bio-information value; a and b denote coefficients obtained by using multi-wavelength pulse wave signals at different pressures, a degree of aging (e.g., physiological age, chronological age, degree of tissue aging, etc.), and the like; and x denotes an independent variable into which the difference $\Delta f$ between the first value $f_1$ and the second value $f_2$ is input.

Figure 5:
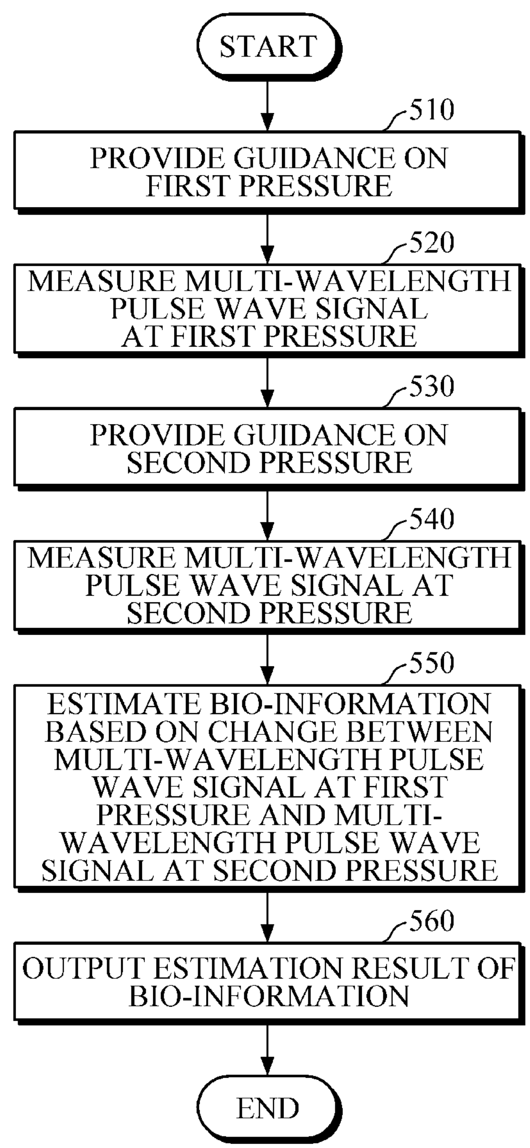
FIG. 5 is a flowchart illustrating a bio-information estimating method according to an example embodiment.
Figure 6:
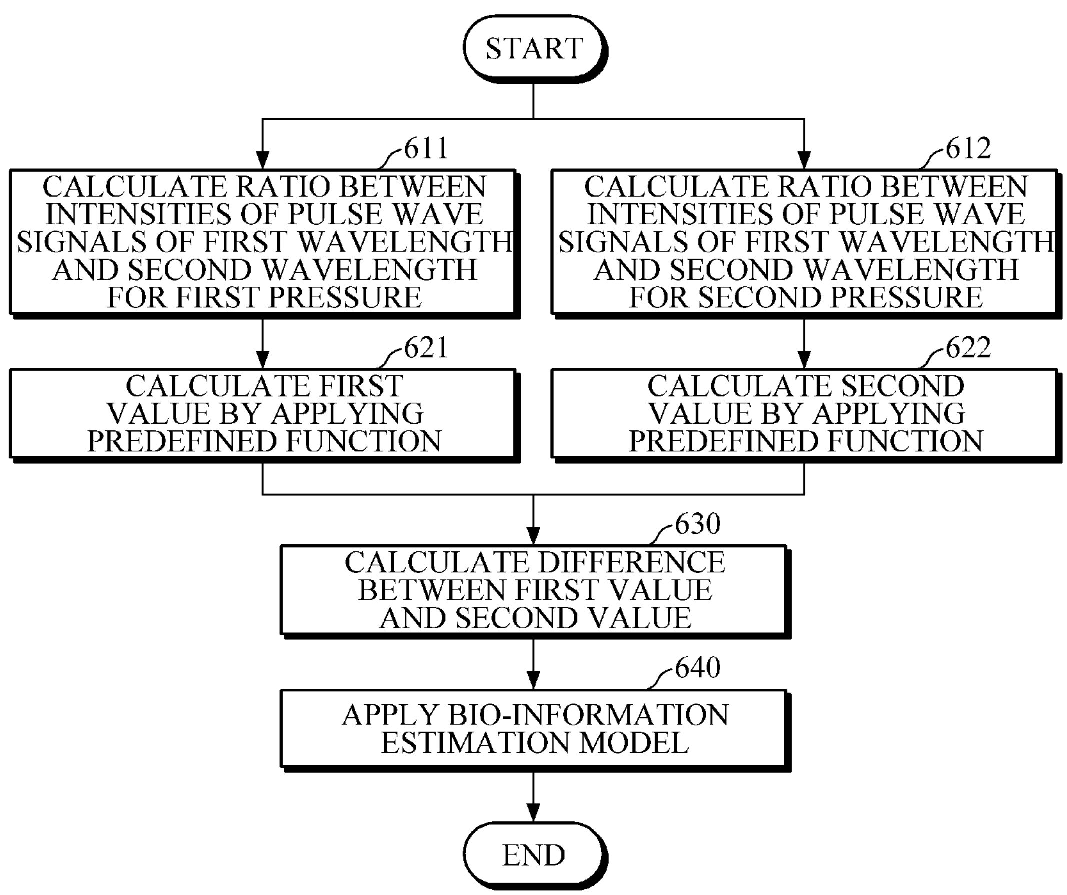
FIG. 6 is a flowchart illustrating an example of estimating bio-information according to an example embodiment.

FIG. 5 is a flowchart illustrating a bio-information estimating method according to an example embodiment. FIG. 6 is a flowchart illustrating an example of estimating bio-information according to an example embodiment. The embodiments of FIGS. 5 and 6 may be an example of a bio-information estimating method performed by the bio-information estimating apparatuses 100*a* and 100*b* of FIG. 1A or 1B.

Upon receiving a request for estimating bio-information, the bio-information estimating apparatus 100*a*/100*b* may provide guidance on a first pressure to a user in operation 510, so that the user may touch a sensor part 110 with an object (e.g., a finger) by applying the first pressure to the sensor part 110 for a first period of time. Here, the first pressure may be contact pressure in a state where the user touches the sensor part 110 with the object without applying any force to the sensor part 110. However, the first pressure is not limited thereto, and may be a contact pressure level higher than or equal to a predetermined threshold. Operation 510 may be omitted in another example embodiment.

Then, the bio-information estimating apparatus 100*a*/100*b* may measure a multi-wavelength pulse wave signal for the first period of time when the user touches the sensor part 110 with the object and applies the first pressure to the sensor part 110 according to the guidance in operation 520. In particular, the multiple wavelengths may include two or more of an infrared wavelength, a blue wavelength, a green wavelength, and a red wavelength.

Subsequently, the bio-information estimating apparatus 100*a*/100*b* may provide guidance on a second pressure to the user in operation 530, so that the user exerts the second pressure to the sensor part 110 by using the object for a second period of time after a lapse of the first period of time. Here, in the case where the first pressure is contact pressure in a state where the object applies no force, the second pressure may be a contact pressure level higher than or equal to a predetermined threshold. By contrast, in the case where the first pressure is a contact pressure level higher than or equal to a predetermined threshold, the second pressure may be contact pressure in a state where the object applies no force.

Next, the bio-information estimating apparatus 100*a*/100*b* may measure a pulse wave signal of multiple wavelengths for the second period of time when the object applies the second pressure to the sensor part 110 according to the guidance in operation 540. In particular, the multiple wavelengths measured in operations 520 and 540 may be the same as each other.

Then, the bio-information estimating apparatus 100*a*/100*b* may estimate a change between the multi-wavelength pulse wave signals which are measured in operations 520 and 540, and may estimate bio-information based on the estimated change in operation 550.

For example, referring to FIG. 6, the bio-information estimating apparatus 100*a*/100*b* may calculate a ratio, in operation 611, between the intensities of the pulse wave signals of the first wavelength and the second wavelength for the first pressure which are measured in 520, and may calculate a first value by inputting the calculated ratio into a predefined function. (e.g., logarithmic function) operation 621. Likewise, the bio-information estimating apparatus 100*a*/100*b* may calculate a ratio, in operation 612, between the intensities of the pulse wave signals of the first wavelength and the second wavelength for the second pressure which are measured in 540, and may calculate a second value by inputting the calculated ratio into a predefined function (e.g., logarithmic function) in operation 622.

The bio-information estimating apparatus 100*a*/100*b* may extract a DC component of each time from the pulse wave signal of each wavelength, and may obtain a mean value of the extracted DC components of each time as the intensities of the pulse wave signals in operations 621 and 622. However, the intensity of the pulse wave signal is not limited to the mean value, but a median value, a maximum value, a minimum value, a mode, a linear combination result, and the like may also be obtained as the intensity of the pulse wave signal.

Subsequently, upon calculating the first value and the second value in operations 621 and 622, the bio-information estimating apparatus 100*a*/100*b* may calculate a difference between the first value and the second value, to obtain a pulse wave signal change for the first pressure and the second pressure in operation 630.

Next, the bio-information estimating apparatus 100*a*/100*b* may estimate bio-information by inputting the calculated difference between the first value and the second value into the bio-information estimation model as represented by the above Equation 2 in operation 640.

Referring back to FIG. 5, upon estimating bio-information in operation 550, the bio-information estimating apparatus 100*a*/100*b* may output an estimation result of bio-information in operation 560. For example, the bio-information estimating apparatus 100*a*/100*b* may output the estimation result of bio-information in various visual manners using a visual output device such as a display and the like. Alternatively, the bio-information estimating apparatus 100*a*/100*b* may provide the estimation result of bio-information in a non-visual manner through voice, tactile sensation, vibrations, and the like using a speaker and/or a haptic module. Further, the bio-information estimating apparatus 100*a*/100*b* may determine a user's health condition based on the estimated bio-information, and may provide guidance information, such as a warning or a response action, to a user based on the determination.

Figure 7:
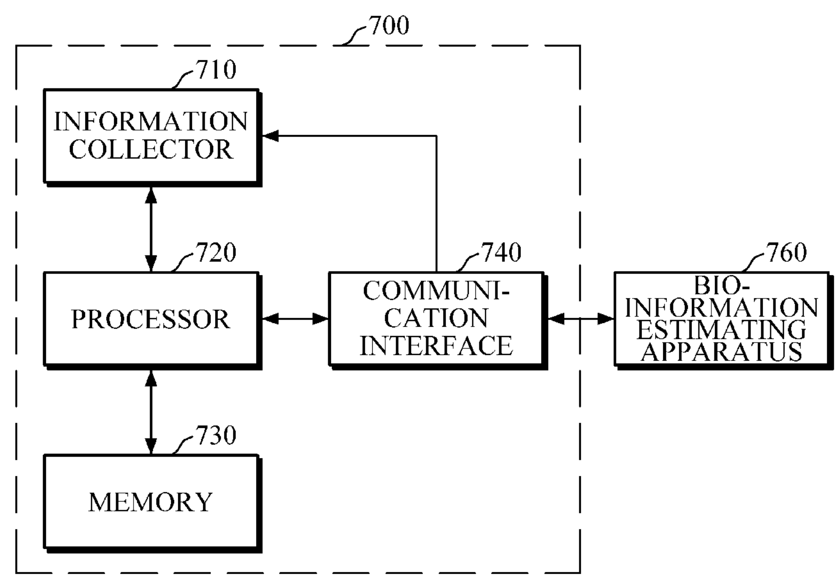
FIG. 7 is a block diagram illustrating an apparatus for supporting estimation of bio-information according to an example embodiment.
Figure 8A:
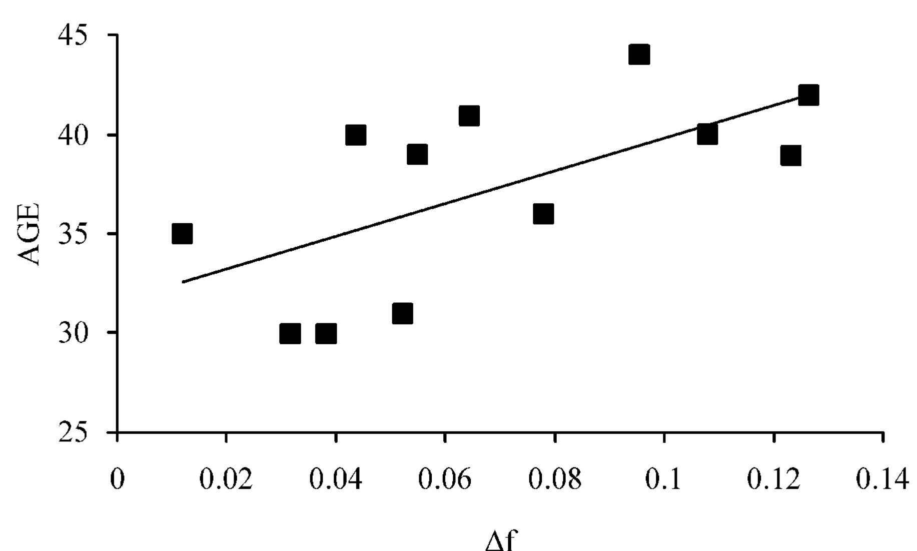
FIGS. 8A and 8B are diagrams illustrating examples of a bio-information estimation model.
Figure 8B:
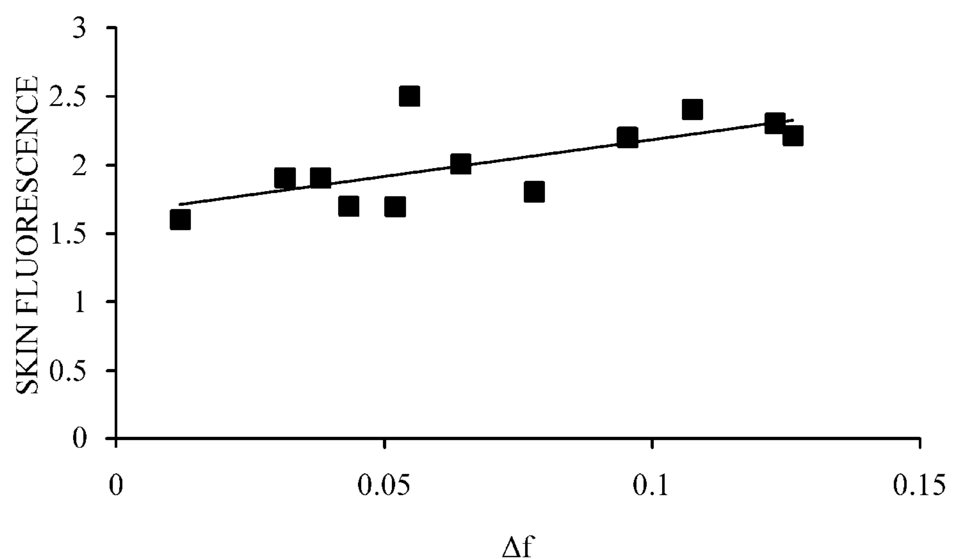

FIG. 7 is a block diagram illustrating an apparatus for supporting estimation of bio-information according to an example embodiment. FIGS. 8A and 8B are diagrams illustrating examples of a bio-information estimation model. The apparatus 700 for supporting estimation of bio-information may be embedded in an electronic device, such as a smartphone, a tablet PC, a desktop computer, a laptop computer, and the like, in a server of a manufacturer or a seller of the apparatus 700, or in a medical device manufactured for use in medical institutions to measure or analyze bio-information. The apparatus 700 for supporting estimation of bio-information may perform various functions of supporting a bio-information estimating apparatus 760. For example, the apparatus 700 for supporting estimation of bio-information may generate and update a bio-information estimation model, and may distribute the bio-information estimation model to the bio-information estimating apparatus 760.

Referring to FIG. 7, the apparatus 700 for supporting estimation of bio-information includes an information collector 710, a processor 720, a memory 730, and a communication interface 740.

The information collector 710 may collect multi-wavelength pulse wave signals for first pressure, multi-wavelength pulse wave signals for second pressure, and information on a degree of aging from a plurality of users. In particular, the information on a degree of aging may include a biological age and/or skin fluorescence of a user.

For example, the information collector 710 may be connected to the bio-information estimating apparatuses 760, used by the plurality of users, through the communication interface 740, and may collect various types of information from the bio-information estimation apparatuses 760. Alternatively, the information collector 710 may obtain multi-wavelength pulse wave signals at the first pressure and the second pressure, which are different from each other, from the plurality of users participating in an experiment and information on a degree of aging of the users. To this end, the apparatus 700 for supporting estimation of bio-information may be configured to perform the function of the bio-information estimating apparatus described above. Further, the information collector 710 may collect skin fluorescence information from the plurality of users by using a device (AGE reader) for measuring the skin fluorescence information.

Based on the multi-wavelength pulse wave signals at the first pressure and the second pressure which are collected from the plurality of users, the processor 720 may estimate a change between the multi-wavelength pulse wave signal at the first pressure and the multi-wavelength pulse wave at the second pressure for each of the users.

For example, as described above, the processor 720 may calculate a ratio between the intensity of a pulse wave signal of a first wavelength and the intensity of a pulse wave signal of a second wavelength for the first pressure, and may obtain a first value by inputting the calculated ratio into a predefined function (e.g., logarithmic function). Likewise, the processor 720 may calculate a ratio between the intensity of a pulse wave signal of a first wavelength and the intensity of a pulse wave signal of a second wavelength for the second pressure, and may obtain a second value by inputting the calculated ratio into a predefined function (e.g., logarithmic function). Upon calculating the first value and the second value for the plurality of users, the processor 720 may estimate a pulse wave signal change by calculating a difference between the first value and the second value.

Upon calculating the difference between the first value and the second value, the processor 720 may analyze a correlation between the calculated difference and a degree of aging based on the collected information on the degree of aging, and may generate an estimation model for estimating a biological age or a degree of tissue aging of a user. For example, referring to FIG. 8A, the processor 720 may obtain a linear regression model for estimating a user's biological age by using a correlation between the difference $\Delta f$ between the first value and the second value for each user and a biological age of each user. Referring to FIG. 8B, by using a correlation between the difference $\Delta f$ between the first value and the second value for each user and skin fluorescence measured from each user, the processor 720 may obtain a linear regression model for estimating a degree of tissue aging.

Based on the collected information on the degree of aging of users, the processor 720 may classify the users into a plurality of groups, e.g., age groups, and may generate a bio-information estimation model for each group.

The processor 720 may distribute the generated bio-information estimation model to the bio-information estimating apparatus 760 through the communication interface 740. In response to a request from a specific bio-information estimating apparatus 760, or determination that it is required to update the bio-information estimating apparatus 700, upon generating a bio-information estimation model or at predetermined intervals, the processor 720 may distribute the generated bio-information estimation model to the bio-information estimating apparatus 760.

The communication interface 740 may communicate with the bio-information estimating apparatus 760 and may receive, from the bio-information estimating apparatus 760, a request for the bio-information estimation model, a pulse wave signal and/or a degree of aging, and the like. Further, the processor 720 may control transmission of the bio-information estimation model to the bio-information estimating apparatus 760.

The memory 730 may store the collected various types of information and/or the generated bio-information estimation model.

Figure 9:
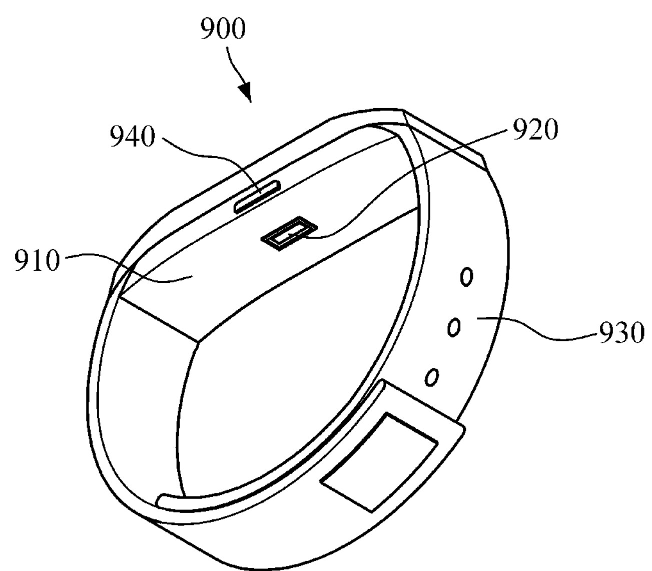
FIG. 9 is a diagram illustrating an example of a wearable device according to an example embodiment.

FIG. 9 is a diagram illustrating a wearable device according to an example embodiment. Various embodiments of the above-described bio-information estimating apparatuses 100*a* and 100*b* may be embedded in a smart watch worn on the wrist or a smart band-type wearable device. However, this is merely exemplary for convenience of explanation, and the bio-information estimating apparatuses 100*a* and 100*b* may be applied to an information processing terminal such as a smartphone, a tablet PC, a laptop computer, a desktop computer, and the like.

Referring to FIG. 9 the wearable device 900 includes a main body 910 and a strap 930.

The main body 910 may be formed to have various shapes, and may include modules which are mounted inside or outside of the main body 910 to perform the aforementioned function of estimating bio-information as well as various other functions. A battery may be embedded in the main body 910 or the strap 930 to supply power to various modules of the wearable device 900.

The strap 930 may be connected to the main body 910. The strap 930 may be flexible, so as to be bent around a user's wrist. The strap 930 may be bent in a manner that allows the strap 930 to be detached from the user's wrist or may be formed as a band that is not detachable. Air may be injected into the strap 930 or an airbag may be included in the strap 930, so that the strap 930 may have elasticity according to a change in pressure applied to the wrist, and the change in pressure of the wrist may be transmitted to the main body 910.

The main body 910 may include a sensor part 920 for measuring a bio-signal. The sensor part 920 may be mounted on a rear surface of the main body 910, which comes into contact with the upper portion of a user's wrist, and may include a light source for emitting light onto the skin of the wrist and a detector for detecting light scattered or reflected from the object. In particular, one or more light sources may be provided to emit light of multiple wavelengths. The sensor part 920 may further include a force sensor for measuring contact pressure applied by the object, and an area sensor.

A processor may be mounted in the main body 910. The processor may be electrically connected to various modules, mounted in the wearable device 900, to control operations thereof. In addition, the processor may estimate bio-information, such as a biological age, a degree of tissue aging, and the like based on a change between multi-wavelength pulse wave signals measured by the sensor part 920 at different pressure values.

In the case where the sensor part 920 includes a contact pressure sensor, the processor may monitor a contact state of the object based on contact pressure between the wrist and the sensor part 920, and may provide guidance on a contact position and/or a contact state to a user through a display.

Further, the main body 910 may include a memory which stores a processing result of the processor and various types of information. In particular, various types of information may include criteria for estimating blood pressure as well as information associated with functions of the wearable device 900.

In addition, the main body 910 may also include a manipulator 940 which receives a control command of a user and transmits the received control command to the processor. The manipulator 940 may include a power button to input a command to turn on/off the wearable device 900.

The display 914 may be mounted on a front surface of the main body 910, and may include a touch panel for touch input. The display 914 may receive a touch input from a user, may transmit the received touch input to the processor, and may display a processing result of the processor.

For example, the display 914 may display guidance information on a first pressure for a first period of time; and after a lapse of the first period of time, the display 914 may display guidance information on a second pressure, which is different from the first pressure, for a second period of time, so that the sensor part 920 may measure multi-wavelength pulse wave signals at different contact pressures. Further, the display 914 may display the estimated bio-information. In particular, the display 914 may display additional information, such as an estimation date of bio-information, a user's health condition, and the like, along with the estimated bio-information. When a user requests detailed information by operating the manipulator 640 or by touching the display 614 for touch input, the display 914 may output detailed information in various manners.

Moreover, a communication interface, provided for communication with an external device such as a mobile terminal of a user, may be mounted in the main body 910. The communication interface may transmit an estimation result of bio-information to an external device, e.g., a user's smartphone, to display the result to a user. However, this is merely exemplary, and the communication interface may transmit and receive various types of necessary information.

Figure 10:
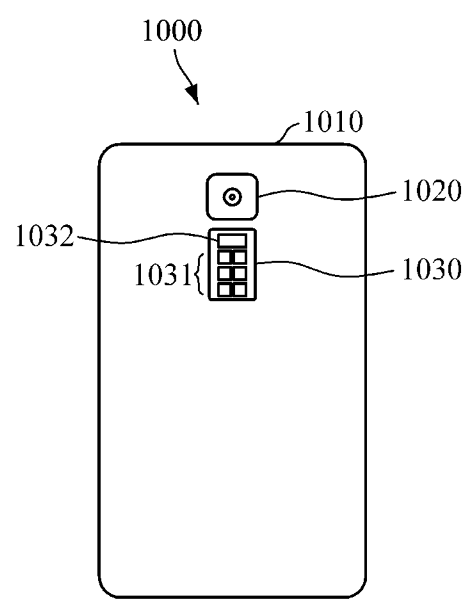
FIG. 10 is a diagram illustrating a smart device according to an example embodiment.

FIG. 10 is a diagram illustrating a smart device, to which embodiments of a bio-information estimating apparatus are applied. In particular, the smart device may be a smartphone, a tablet PC, and the like.

Referring to FIG. 10, the smart device 1000 includes a sensor part 1030 mounted on one surface of a main body 1010. In particular, the sensor part 1030 may include a pulse wave sensor which includes one or more light sources 1031 and a detector 1032. As illustrated in FIG. 10, the sensor part 1030 may be mounted on a rear surface of the main body 1010, but is not limited thereto. Further, the sensor part 1030 may be configured in combination with a fingerprint sensor or a touch panel mounted on a front surface.

In addition, a display may be mounted on a front surface of the main body 1010. The display may visually display an estimation result of bio-information and the like. The display may include a touch panel, and may receive various types of information input through the touch panel and transmit the received information to the processor.

Moreover, an image sensor 1020 may be mounted in the main body 1010. The image sensor 1020 may include a camera and/or a fingerprint scanner. When a user's finger approaches the sensor part 1030 to measure a pulse wave signal, the image sensor 1020 may capture an image of the finger and may transmit the captured image to the processor. In particular, based on the image of the finger, the processor may identify a relative position the finger with respect to an actual position of the sensor part 1030, and may provide the relative position of the finger to the user through the display, so as to guide measurement of pulse wave signals with improved accuracy.

As described above, the processor may estimate bio-information based on the pulse wave signals of multiple wavelengths which are measured by the sensor part 1030 at different pressure values levels. Various modules for performing various other functions may be mounted in the smart device 1000, and detailed description thereof will be omitted.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing example embodiments are merely exemplary and are not to be construed as limiting. The present teaching can be readily applied to other types of apparatuses. Also, the description of the example embodiments is intended to be illustrative, and not to limit the scope of the claims, and many alternatives, modifications, and variations will be apparent to those skilled in the art.

What is claimed is:

1. A bio-information estimating apparatus, comprising:

a sensor part comprising a pulse wave sensor configured to measure a multi-wavelength pulse wave signal, wherein the multi-wavelength pulse wave signal comprises a first pulse wave signal of a first wavelength and a second pulse wave signal of a second wavelength that are measured at a first point in time when a first pressure is applied from an object to the sensor part, and a third pulse wave signal of the first wavelength and a fourth pulse wave signal of the second wavelength that are measured at a second point in time when a second pressure is applied from the object to the sensor part; and a processor configured to extract a direct current (DC) component from the first pulse wave signal and the second pulse wave signal, obtain a statistical value of the DC component as an intensity of each of the first pulse wave signal and the second pulse wave signal, and estimate bio-information based on a difference between a first value representing a first ratio between the intensity of the first pulse wave signal and the intensity of the second pulse wave signal at the first pressure, and a second value representing a second ratio between an intensity of the third pulse wave signal and an intensity of the fourth pulse wave signal at the second pressure.

2. The bio-information estimating apparatus of claim 1, wherein the pulse wave sensor comprises a light source configured to emit light of multiple wavelengths onto the object, and a detector configured to detect light scattered or reflected from the object.

3. The bio-information estimating apparatus of claim 1, wherein one of the first pressure and the second pressure comprises contact pressure between the sensor part and the object, which occurs when the object touches the sensor part without pressing down the sensor part.

4. The bio-information estimating apparatus of claim 1, wherein the processor is further configured to obtain the first value and the second value by applying a predetermined function to the first ratio and the second ratio, respectively, and wherein the predetermined function comprises at least one of a logarithmic function and a linear combination function.

5. The bio-information estimating apparatus of claim 1, wherein the processor is further configured to obtain the first value and the second value by applying a predefined function to the first ratio and the second ratio, respectively.

6. The bio-information estimating apparatus of claim 5, wherein the first wavelength is shorter than the second wavelength.

7. The bio-information estimating apparatus of claim 1, wherein the processor is further configured to apply a bio-information estimation model to the difference between the first value and the second value to obtain aging information of the object.

8. The bio-information estimating apparatus of claim 1, wherein the bio-information comprises at least one of a degree of skin tissue aging and a biological age of the object.

9. The bio-information estimating apparatus of claim 1, wherein the processor is further configured to provide guidance on at least one of the first pressure, the second pressure, and contact pressure between the object and the pulse wave sensor.

10. The bio-information estimating apparatus of claim 9, wherein the processor is further configured to:

upon receiving a request for estimating the bio-information, guide the object to touch the pulse wave sensor with the first pressure for a first period of time; and after a lapse of the first period of time, guide the object to touch the pulse wave sensor with the second pressure for a second period of time.

11. The bio-information estimating apparatus of claim 9, wherein the processor is further configured to obtain the contact pressure between the object and the pulse wave sensor, and provides guidance on the contact pressure.

12. The bio-information estimating apparatus of claim 11, wherein the sensor part further comprises a force sensor configured to measure an intensity of force applied by the object when the object touches the pulse wave sensor, and an area sensor configured to measure a contact area between the object and the pulse wave sensor, wherein the processor is further configured to obtain the contact pressure based on the intensity of the force and the contact area.

13. A bio-information estimating method, comprising:

measuring a first multi-wavelength pulse wave signal that comprises a first pulse wave signal of a first wavelength and a second pulse wave signal of a second wavelength, at a first point in time when a first pressure is applied from an object to a sensor;

measuring a second multi-wavelength pulse wave signal that comprises a third pulse wave signal of the first wavelength and a fourth pulse wave signal of the second wavelength, at a second point in time when a second pressure is applied from the object to the sensor;

extracting a direct current (DC) component from the first pulse wave signal and the second pulse wave signal;

obtaining a statistical value of the DC component as an intensity of each of the first pulse wave signal and the second pulse wave signal; and estimating bio-information based on a difference between a first value representing a first ratio between an intensity of the first pulse wave signal and an intensity of the second pulse wave signal at the first pressure, and a second value representing a second ratio between an intensity of the third pulse wave signal and an intensity of the fourth pulse wave signal at the second pressure.

14. The bio-information estimating method of claim 13, wherein the estimating the bio-information comprises:

obtaining the first value by applying a predefined function to the first ratio; and obtaining the second value by applying the predefined function to the second ratio, wherein the predefined function comprises at least one of a logarithmic function and a linear combination function.

15. The bio-information estimating method of claim 13, further comprising obtaining the first value and the second value by applying a predefined function to the first ratio and the second ratio, respectively.

16. The bio-information estimating method of claim 14, wherein the estimating the bio-information comprises:

applying a bio-information estimation model to the difference between the first value and the second value to obtain aging information of the object.

17. The bio-information estimating method of claim 13, further comprising:

guiding the object to touch a pulse wave sensor with the first pressure for a first period of time; and after a lapse of the first period of time, guiding the object to touch the pulse wave sensor with the second pressure for a second period of time.

18. The bio-information estimating method of claim 13, further comprising:

obtaining contact pressure between the object and a pulse wave sensor; and providing guidance on the contact pressure.

19. The bio-information estimating apparatus of claim 1, wherein the processor is further configured to generate a bio-information estimation model based on a plurality of first multi-wavelength pulse wave signals measured from a plurality of users when the first pressure is applied to the sensor part, a plurality of second multi-wavelength pulse wave signals measured from the plurality of users when the second pressure is applied to the sensor part, and information on a degree of aging of the plurality of users.

20. The apparatus of claim 19, wherein for the plurality of users, the processor is further configured to obtain the first value and the second value by applying a logarithmic function to the first ratio and the second ratio, respectively, and generate the bio-information estimation model by analyzing a correlation between the difference between the first value and the second value and the degree of aging.

* * * * *